Figure 9:
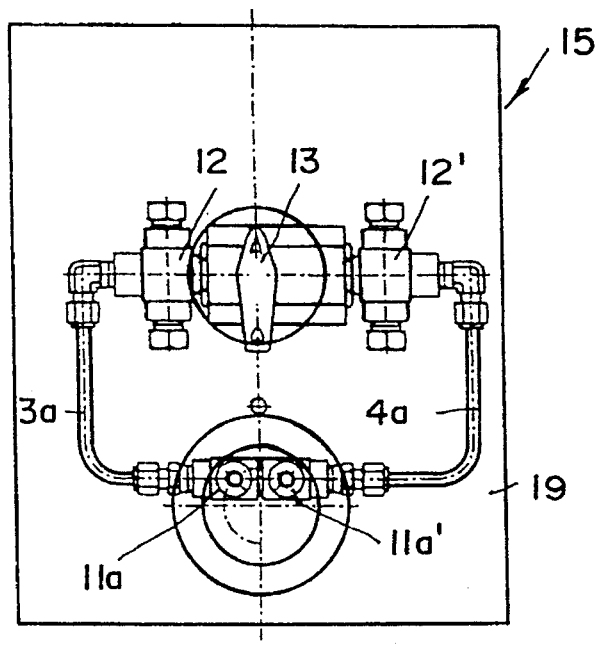

United States Patent [19]
Jansen

[11] Patent Number: 5,594,182
[45] Date of Patent: Jan. 14, 1997

[54] APPARATUS FOR TAKING A SAMPLE OF A FLUID AND PART FOR SUCH AN APPARATUS

[75] Inventor: Adolf E. Jansen, Rotterdam, Netherlands

[73] Assignee: Dobart Holding B.V., Rotterdam, Netherlands

[21] Appl. No.: 393,484

[22] Filed: Feb. 24, 1995

[30] Foreign Application Priority Data

Feb. 25, 1994 [NL] Netherlands ............... 9400291

[51] Int. Cl.$^6$ ............................................. G01N 1/10
[52] U.S. Cl. ............................................. 73/863.71
[58] Field of Search ........................ 73/863.71, 863.72, 73/863.83

[56] References Cited

U.S. PATENT DOCUMENTS

| | | | |
|---|---|---|---|
| 4,993,271 | 2/1991 | Vargason | 73/863.33 |
| 5,131,282 | 7/1992 | Kuhner | 73/863.71 |

*Primary Examiner*—Robert Raevis
*Attorney, Agent, or Firm*—Beveridge, DeGrandi, Weilacher & Young

[57] ABSTRACT

Apparatus for taking a sample of a fluid. The apparatus contains a sampling station and a part which can be uncoupled therefrom, in Which a sampling bomb space and a four-way cock are integrated. The sampling station contains a first sample supply sub conduit with coupling element and a first sample discharge sub conduit with coupling element. The part further contains a second sample supply sub conduit with coupling element, a second sample discharge sub conduit with coupling element, and a sampling bomb supply and sampling bomb discharge conduit arranged between the four-way cock and the sampling bomb space. In a first position of the four-way cock the sampling bomb conduits are connected to each other and the second sub conduits to each other. In a second position of the four-way cock, suitable for taking a sample, the second sample supply sub conduit is connected to the sampling bomb supply conduit and the sampling bomb discharge conduit with the second sample discharge sub conduit. The part for use in the apparatus preferably has a cock knob with spring-back mechanism.

11 Claims, 4 Drawing Sheets

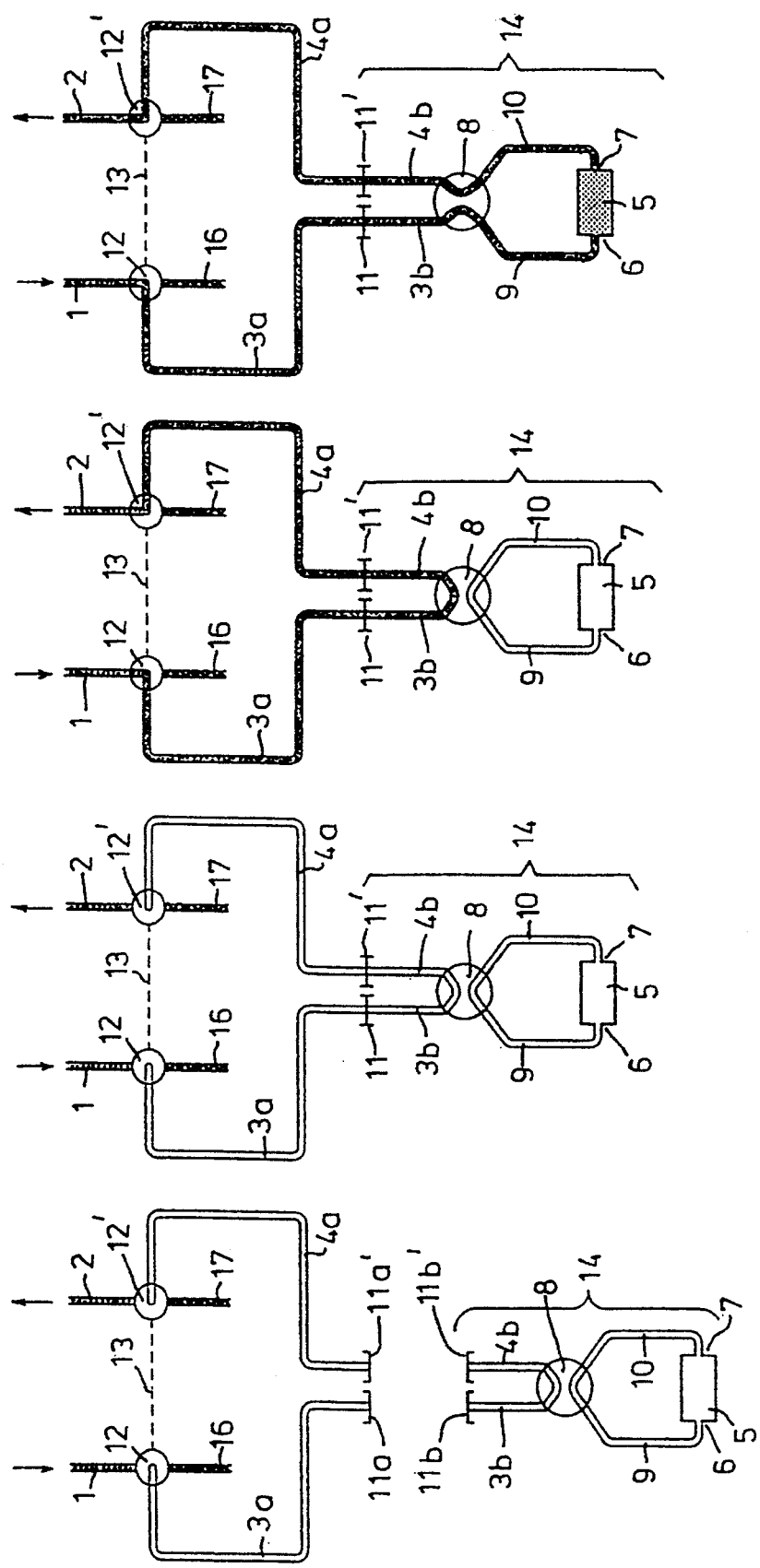

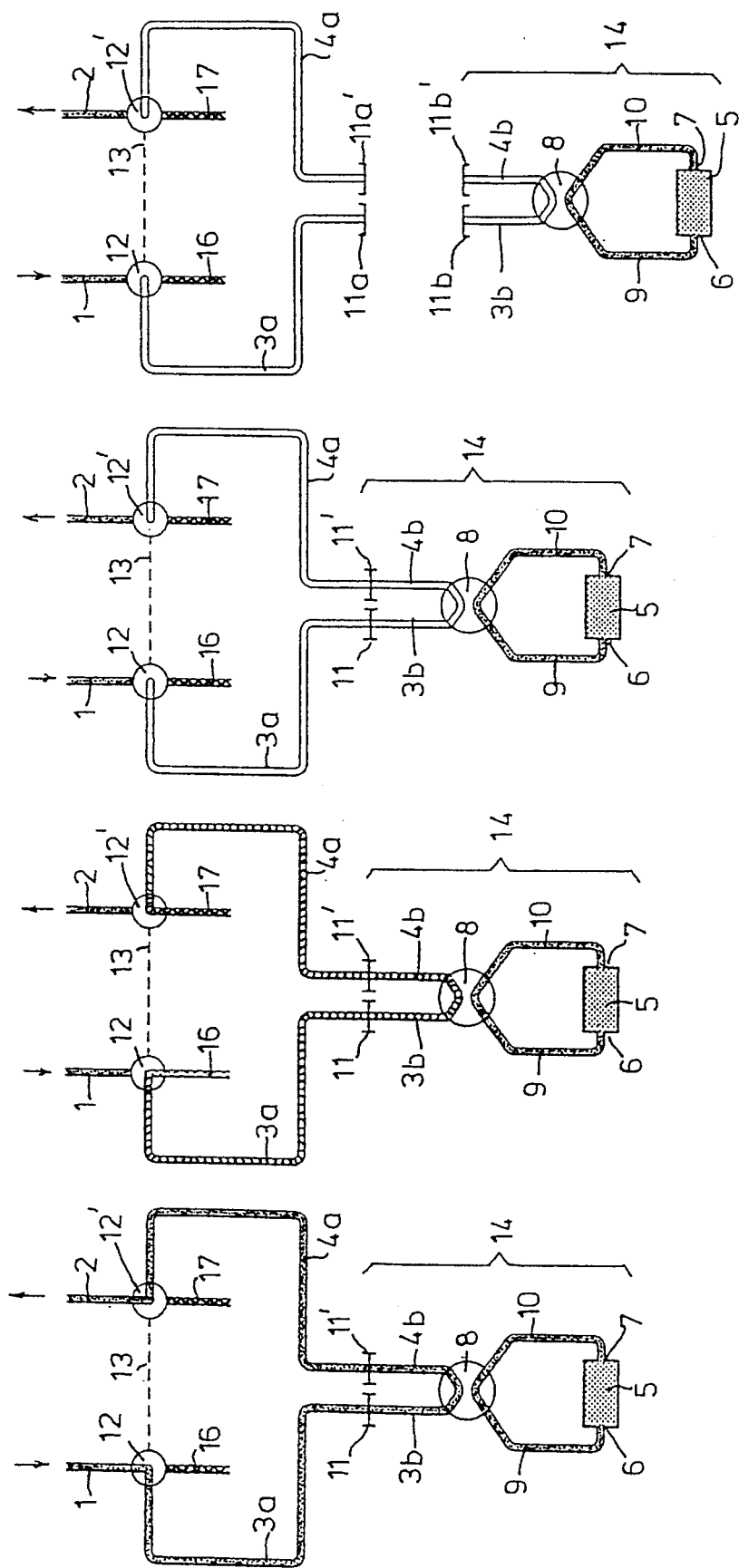

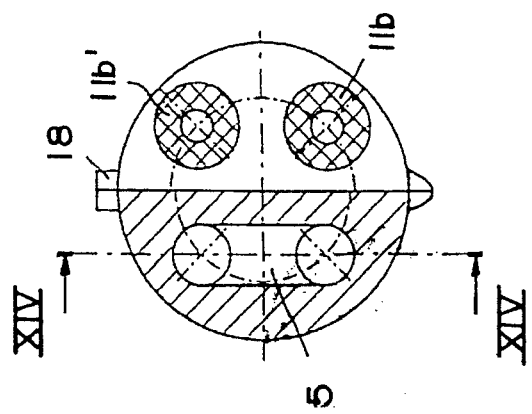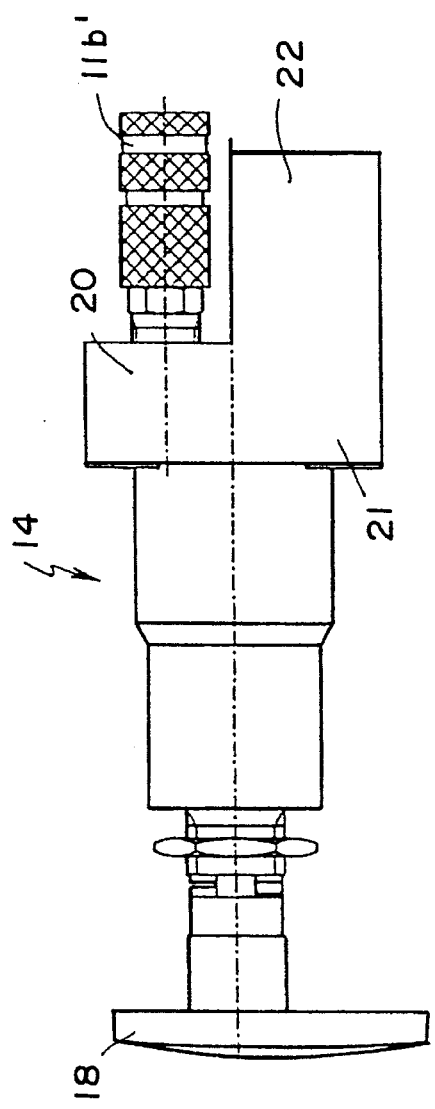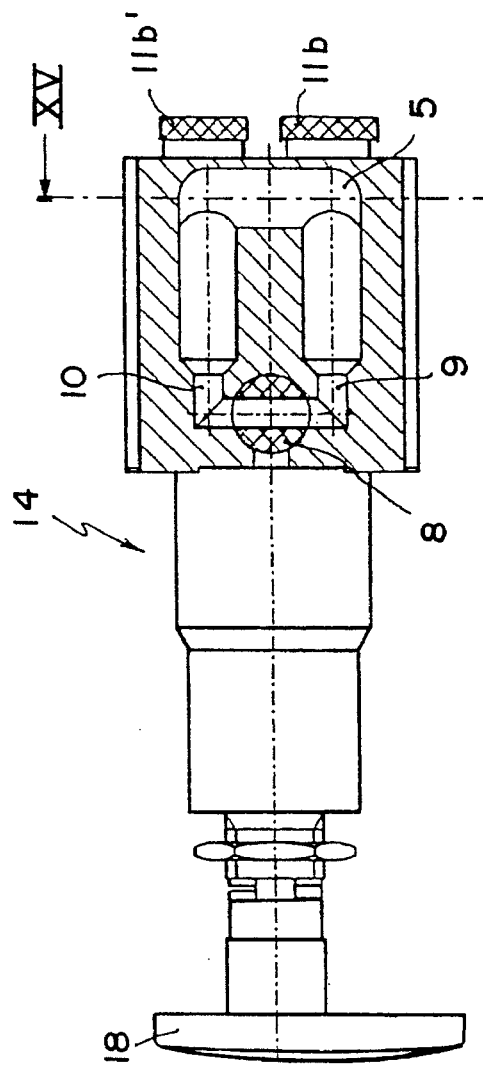

APPARATUS FOR TAKING A SAMPLE OF A FLUID AND PART FOR SUCH AN APPARATUS

The invention relates to an apparatus for taking a sample of a fluid enclosed in a container, which apparatus is provided with a sampling station which is connectable to the container via a fluid supply conduit and a fluid discharge conduit, with a sample supply conduit and a sample discharge conduit, with a sampling bomb for containing the fluid sample, which sampling bomb comprises a sampling bomb space, a sampling bomb supply opening and a sampling bomb discharge opening, which are connectable to the sample supply conduit and the sample discharge conduit, respectively, and with a four-way cock, in one of the two positions of the four-way cock the fluid supply conduit being connected to the sampling bomb supply opening and the fluid discharge conduit being connected to the sampling bomb discharge opening.

The invention also relates to a part for use in such a apparatus.

Such an apparatus is known from the European patent specification EP-0.224.692-B1. This known apparatus contains a sampling station with a four-way cock. Two gates of the four-way cock are connected to a fluid supply conduit and a fluid discharge conduit which can be connected to the container by means of cocks or valves. The two other gates of the four-way cock are connected to a sample supply conduit and a sample discharge conduit, which are both provided with coupling elements at their free ends. In a first position of the four-way cock the fluid supply conduit is connected to the fluid discharge conduit and the sample supply conduit is connected to the sample discharge conduit. In the second position of the four-way cock the fluid supply conduit is connected to the sample supply conduit and the fluid discharge conduit is connected to the sample discharge conduit. The apparatus is further provided with a sampling bomb with a sampling bomb supply opening, a sampling bomb discharge opening and a sampling bomb space, wherein the sampling bomb supply opening and the sampling bomb discharge opening can be shut off from the sampling bomb space by means of revolving valves. The sampling bomb supply opening and sampling discharge opening are provided with coupling elements which belong to the coupling elements of the sample supply conduit and the sample discharge conduit. The apparatus also contains a rinsing apparatus with a supply conduit with cocks or valves which opens into the sample discharge conduit near the end thereof and with a discharge conduit with cocks or valves which opens into the sample supply conduit near the end thereof. Prior to taking a sample the four-way cock of the sampling station is in the first position. The sampling bomb is then coupled to the sampling station, after which the fluid can flow through the sample bomb space by placing the four-way cock in the second position and opening the revolving valves. After closing the revolving valves and setting the four-way cock in the first position, there is a sample of the fluid in the sampling bomb space. Subsequently the sample supply conduit and the sample discharge conduit are rinsed with the help of the rinsing apparatus with a rinsing medium, for removing the fluid to be sampled which can, for example, be HF from the sample supply conduit. After that the sample bomb and the sample discharge conduit can be uncoupled. It might also be possible to rinse the sample bomb space before setting the four-way cock in the second position. Although this apparatus is able to sample easily evaporable, possibly poisonous fluids in an emission-free way, there is a risk, because of the relatively high number of operations which have to be carried out for taking a sample, that one of these operations is forgotten or that the correct sequence of actions can be deviated from, as a result of which, for example, a quantity of fluid can escape or a sample is obtained which is not representative for the fluid. Besides, because of the complex rinsing apparatus, rinsing the sample supply conduit and the sample discharge conduit is laborious and time-consuming.

It is an object of the present invention to provide an apparatus for taking a sample of a fluid enclosed in a container which is of simple construction and simple to use, a high level of safety being guaranteed when taking a sample.

It is a further object of the present invention to provide an apparatus for taking a sample of a fluid enclosed in a container, wherein the rinsing of the appropriate conduits can also take place in a simple way.

For this purpose an apparatus of the sort named in the opening paragraph is characterized, in that the sampling bomb supply opening and the sampling bomb discharge opening, are firmly connected to the four-way cock by a sampling bomb supply conduit and a sampling discharge conduit, respectively, that the sample supply conduit and the sample discharge conduit are connected to the four-way cock, that the sample supply conduit as well as the sample discharge conduit contain two detachable sub conduits, and that the sub conduits which are not connected to the four-way cock are connectable to the fluid supply conduit and the fluid discharge conduit, in the one position of the four-way cock the sample supply sub conduit which is connected to the four-way cock being connected to the sample discharge sub conduit which is connected to the four-way cock and the sampling bomb supply conduit with the sampling bomb discharge conduit, and in the other position of the four-way cock the sample supply sub conduit which is connected to the four-way cock being connected to the sampling bomb supply conduit and the sample discharge sub conduit which is connected to the four-way cock being connected to the sampling bomb discharge conduit. In this way it is possible to obtain a sample of the fluid by only operating the four-way cock, as a result of which the ease of operation is improved and the chance that the apparatus is wrongly operated is reduced considerably.

An embodiment of an apparatus is characterized in that the sub conduits are detachably connected to each other by rapid-action couplings for forming the sample supply conduit and the sample discharge conduit. In this way coupling and uncoupling of the sub conduits, in other words of the sample bomb space and the container, is practicable in a simple and reliable way. Preferably the rapid-action couplings are formed by coupling elements which, when detaching, shut off the sub conduits concerned. In this way an additional safety measure against escape of the fluid to be sampled is provided.

When the four-way cock is a four-way ball valve, a hermetical closure of the cock can be obtained in a simple way.

A preferred embodiment of an apparatus according to the invention is characterized in that the sub conduits of the sample supply conduit and the sample discharge conduit which are not connected to the four-way cock are each connectable by a multi-stage cock with at least three gates to the fluid supply conduit and the fluid discharge conduit, respectively. In this way, in a simple and reliable way, a coupling with one or more rinsing apparatuses is possible, which can rinse the sample supply conduit and the sample discharge conduit and possibly also the sampling bomb space, the sampling bomb supply conduit and the sampling discharge conduit. Moreover, in this way more than one container can be coupled to the sampling station by the multi-stage cock.

When both multi-stage cocks have a common control, a rinsing can be obtained by activating only the common control, so that the operation of the apparatus is user-friendly.

A preferred embodiment of an apparatus according to the invention is characterized in that the sampling bomb, the sampling bomb supply conduit and the sampling bomb discharge conduit, the four-way cock and the sub conduits of the sample supply conduit and the sample discharge conduit which are connected to the four-way cock are integrated in one part. By doing this a mechanically stable unit of the elements incorporated in that part is formed, so that a good attachment of that part to the sampling station is obtained and the sample taken can be transported in the part. It is noted that the sampling station is formed by the sub conduits of the sample supply conduit and the sample discharge conduit which are not connected to the four-way cock, and possibly, the multi-stage cocks with a rinsing apparatus.

The invention also relates to a part for use in an apparatus according to the present invention, the part being provided with the sampling bomb, the sampling bomb supply conduit and the sampling bomb discharge conduit, the four-way cock and the sub conduits of the sample supply conduit and the sample discharge conduit connected to the four-way cock. This part is extremely suited for attaching to the sampling station for obtaining a sample of the fluid as well as for containing and transporting the sample.

When the part contains a cock knob for operating the four-way cock, which cock knob is provided with a spring-back mechanism, the four-way cock is always in the one position if the cock knob is not operated, as a result of which the sampling bomb space is shut off from the surroundings.

Figure 10:
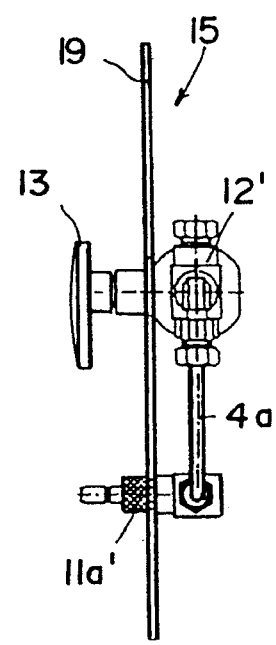
Figure 11:
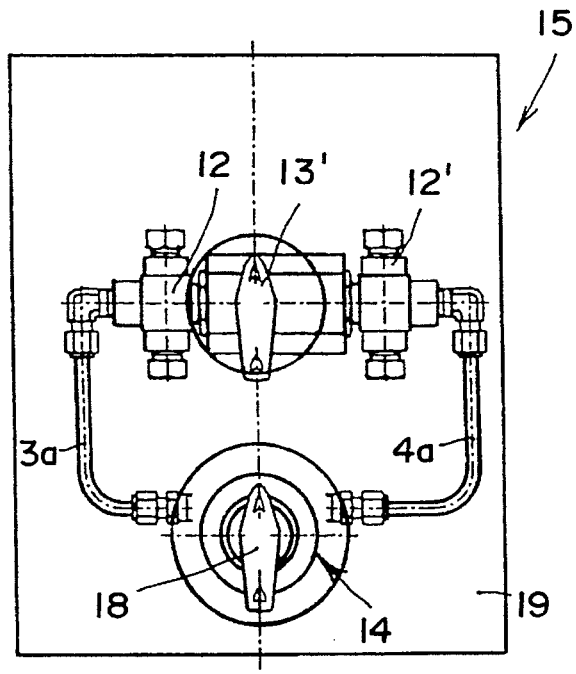
Figure 12:
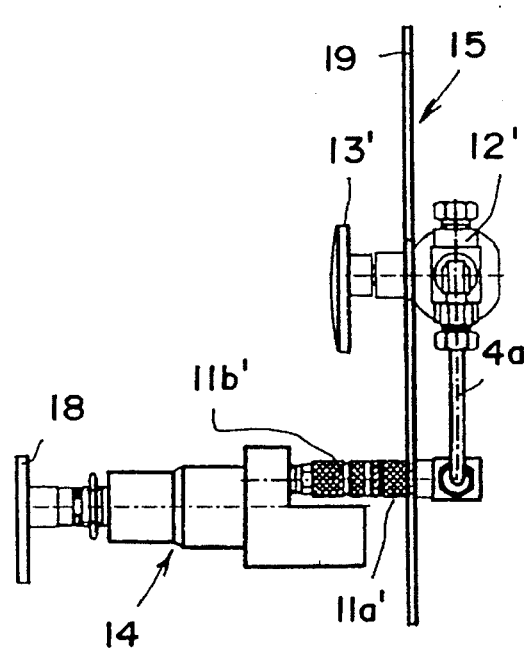

An embodiment of an apparatus and part according to the invention will be discussed by way of example with reference to the drawing. In the drawing FIGS. 1–8 schematically show an apparatus according to the invention in different stages of the sampling of a fluid and the rinsing of elements of the apparatus;

FIGS. 9 and 10 shows a front and a side view, respectively, of a sampling station of an apparatus according to the present invention, FIGS. 11 and 12 show a front and a side view, respectively, of a sampling station and a part according to the invention in a coupled state, FIG. 13 shows a view of a part according to the invention, and FIGS. 14 and 15 show a bottom and a front view, respectively, partially in cross section, of a part according to the invention.

In FIG. 1 an apparatus for taking a sample of a fluid is shown schematically. The fluid is enclosed in a container, which can be a tank or a processing installation, for example.

Examples of fluids to be sampled are easily evaporable substances such as HF, HCl, HBr, organic substances such as hydrocarbons, and gases which are in the fluid phase at surrounding temperatures.

The apparatus is provided with a sampling station which is connectable to the container via a fluid supply conduit 1 and the fluid discharge conduit 2. In this embodiment the sampling station contains two three-way cocks 12, 12', which are connected to the fluid supply conduit 1 and fluid discharge conduit 2, respectively. In another embodiment in which, for example, two containers are to be sampled by the sampling station, the three-way cocks can be replaced by multi-stage cock with more than three gates. In addition the sampling station contains a first sub conduit 3a of the sample supply conduit which is connected to the three-way cock 12 and a first sub conduit 4a of a sample discharge conduit which is connected to the three-way cock 12'. The sampling station moreover contains a supply 16 and a discharge 17 of a rinsing apparatus, which can be of every known type. The ends of the first sub conduits 3a and 4a are provided with coupling elements, preferably rapid-action coupling elements 11a and 11a'.

The apparatus is further provided with a sampling bomb, which contains a sampling bomb space 5, a sampling bomb supply opening 6 and a sampling bomb discharge opening 7. The sampling bomb supply opening 6 and the sampling bomb discharge opening 7 can be connected via a sampling bomb supply conduit 9 and a sampling discharge conduit 10, respectively, with two gates of a four-way cock 8. The other two gates of the four-way cock 8 can be connected to the second sub conduit 3b of the sample supply conduit and the second sub conduit 4b of the sample discharge conduit. The ends of the second sub conduits 3b and 4b are provided with coupling elements, preferably rapid-action couplings elements 11b and 11b' which can be coupled with the rapid-action coupling elements 11a and 11a' respectively.

The four-way cock 8 can take up two positions. In the first position of the four-way cock 8 the sub conduit 3b is connected to the sub conduit 4b and the sample supply conduit 9 to the sample bomb discharge conduit 10. In the second position of the four-way cock 8 the sub conduit 3b is connected to the sample bomb supply conduit 9 and the sub conduit 4b to the sample discharge conduit 10.

In the situation shown in FIG. 1 the rapid-action coupling elements 11a, 11a' are uncoupled from the rapid-action elements 11b, 11b', the three-way cocks 12 and 12' are in their closed position and the four-way cock 8 is in the first position. As a result it is realized that the sample bomb space 5 for containing the sample is shut off by the four-way cock 8 from the surroundings, and the rinsing apparatus and the container are shut off by the three-way cocks 12 and 12' from the surroundings. In order to prevent further potential leakages to the surroundings, the rapid-action coupling elements 11a, 11b, 11a', 11b' are preferably of the type which, when uncoupling, shuts off the sub conduits in question to which they are attached, this shutting off being discontinued when the elements are coupled. A further protection against leakage is furnished by using a four-way ball valve 8, the gates connecting the gates two by two via two channels in the ball.

From the initial position in FIG. 1 the coupling elements 11a and 11a' are coupled to the coupling elements 11b and 11b', so that the situation in FIG. 2 arises.

Subsequently the three-way cocks 12 and 12' are set in a position in which the fluid supply conduit 1 is connected to the sample supply sub conduit 3a and the fluid discharge conduit 2 is connected to the sample discharge sub conduit 4a. The three-way cocks 12, 12' can be operated by separate cock knobs, but the three-way cocks 12, 12' are preferably operated with the help of a common control 13. To this end the three-way cocks 12, 12' are connected to each other, for example by a gear box so that one operating knob sets the cocks in the same position. In order to guarantee a correct sequence of actions this common operating knob is preferably only rotatable in one direction. In this situation, as shown in FIG. 3, the fluid to be sampled is in the sample supply conduit 3a, 3b and sample discharge conduit 4a, 4b.

After that the four-way cock 8 is set in the second position, FIG. 4, so that the fluid to be sampled can flow through the sampling bomb supply conduit 9, the sampling bomb space 5 and the sampling bomb discharge conduit 10. Bringing the four-way cock 8 into the second position can be realized by operating a separate cock knob belonging to the four-way cock 8.

Subsequently the four-way cock 8 is brought into the first position again, as a result of which the sample bomb space 5 filled with a sample of the fluid is shut off from the sample supply sub conduit 3b and sample discharge sub conduit 4b (FIG. 5).

Before the coupling elements can be uncoupled from each other, the sample supply conduit 3a, 3b and the sample discharge conduit 4a, 4b should be rinsed with a suitable rinsing medium, to prevent that the potentially poisonous fluid escapes into the surroundings. For this purpose the three-way cocks 12 and 12' are set (FIG. 6), such that the sample supply sub conduit 3a is connected to the supply 16 for the rinsing medium and the sample discharge sub conduit 4a with the discharge 17 for the rinsing medium. Rinsing takes place during a period which is sufficient so that all the fluid present in the sub conduits 3a, 3b, 4a, 4b is displaced by the rinsing medium.

Subsequently the three-way cocks 12, 12' are brought into their closed position (FIG. 7), after which the coupling elements 11a, 11b and 11a', 11b' are uncoupled from each other (FIG. 8). In this way a sample of the fluid in the sampling bomb space 5 is obtained in a quick and safe way.

Generally the sample is tested in a testing laboratory so that the sample has to be transported. For ensuring that this transport is made possible without any further operations, it is preferable if the sample bomb space 5, the sample bomb supply conduit 9, the sample bomb discharge conduit 10, the four-way cock 8 and the sub conduits 3b and 4b, including their rapid-action coupling elements 11b and 11b' are integrated in one part 14 In this way, moreover, a mechanically stable part 14 can be obtained, in which the sampling bomb space 5 is also hermetically shut off from the surroundings.

From the point of view of mechanical stability and, in the case of using different containers in the apparatus according to the invention, such as processing installations, it is preferable to furnish the sampling station 15 as modular unit (FIGS. 9 and 10). For this purpose the two three-way cocks 12, 12' the sample supply sub conduit 3a including rapid-action element 11a, the sample discharge sub conduit 4a including rapid-action element 11a' and the common control 13, are, for example, mounted on a plate 19 or alternatively in a cabinet. The sampling station 15 can be coupled in a straightforward way via the three-way cocks 12, 12' to each processing installation and rinsing apparatus.

The part 14 can easily be coupled to the sampling station 15, such as is shown in front view in FIG. 11 and in side view in FIG. 12. In the embodiment shown in FIGS. 9, 10, 11 and 12 the part 14 has a separate cock knob 18 for operating the four-way cock and the sampling station 15 and operating knob 13' for the three-way cocks 12, 12'.

The part 14 for use in an apparatus according to the invention is shown schematically in elevation in FIG. 13 and in part in cross section in FIGS. 14 and 15. In this embodiment the part 14 has a cylindrical form, the two rapid-action elements 11b, 11b' projecting from a cylinder half 20 and the sampling bomb space 5 is in a half cylinder-shaped part 22 which projects from the other cylinder half 21. The whole is, for example, made of stainless steel, other steel alloys or materials which are suited for use in this part. Preferably the cock knob 18 is provided with a spring-back mechanism which always brings the cock knob 18, which is in an non-operated position, into the position in which the sampling bomb space 5 is shut off from the surroundings.

Thus according to the invention an apparatus is provided for taking a sample of a fluid, as well as a part to be used therein, in which according to the invention a sampling bomb is integrated with a four-way cock, which allows the taking and transporting of a sample in a simple and safe way. It will be clear that the invention is not restricted to the embodiments described above. Thus it is also possible that the part is constructed in such a way that the cock knob with spring-back mechanism is omitted of. Instead the operating axis of the cock can, together with the rapid-action couplings, be directly or indirectly coupled to an additional outgoing axis from the gear box, so that control of the multi-stage cocks of the sampling station can also contain the desired control of the four-way cock of the part. Instead of the spring-back mechanism for the cock knob the four-way cock can be connected to another mechanism which guarantees the closing of the sample bomb space from the surroundings when uncoupling the part and the sampling station. It is also possible to rinse the sample bomb space with a rinsing medium prior to the situation shown in FIG. 3 by appropriate operation of the three-way cocks and the four-way cock. As a safety measure each cock can further be provided with a lock, as a result of which operation can only take place after unlocking the lock using a fitting key.

I claim:

1. Apparatus for taking a sample of a fluid enclosed in a container, which apparatus is provided with a sampling station which is connectable to the container via a fluid supply conduit and a fluid discharge conduit, with a sample supply conduit connected by a fluid supply valve to the fluid supply conduit and a sample discharge conduit connected by a fluid discharge valve to the fluid discharge conduit, with a sampling bomb for containing the fluid sample, which sampling bomb comprises a sampling bomb space, a sampling bomb supply opening and a sampling bomb discharge opening, which are connectable to the sample supply conduit and the sample discharge conduit, respectively, and with a four-way cock, in one of the two positions of the four-way cock the fluid supply conduit being connected to the sampling bomb supply opening and the fluid discharge conduit being connected to the sampling bomb discharge opening, characterized in that the sampling bomb supply opening and the sampling bomb discharge opening are firmly connected to the four-way cock by a sampling bomb supply conduit and a sampling bomb discharge conduit, respectively, that the sample supply conduit is formed by a first sample supply sub conduit having a first end connected to the fluid supply valve and a second end comprising a rapid-action coupling and by a second sample supply sub conduit having a first end with a rapid-action coupling for coupling to the rapid-action coupling of the first sample supply sub conduit and a second end firmly connected to the four-way cock, that the sample discharge conduit is formed by a first sample discharge sub conduit having a first end connected to the fluid discharge valve and a second end comprising a rapid-action coupling and by a second sample discharge sub conduit having a first end with a rapid-action coupling for coupling to the rapid-action coupling of the first sample discharge sub conduit and a second end firmly connected to the four-way cock, each of said rapid-action couplings including a coupling element which shuts off its respective sub conduit when detaching, in a first position of the four-way cock the second sample supply sub conduit which is connected to the four-way cock being connected to the second sample discharge sub conduit which is connected to the four-way cock and the sampling bomb supply conduit with the sampling bomb discharge conduit, and in a second position of the four-way cock the second sample supply sub conduit which is connected to the four-way cock being connected to the sampling bomb supply conduit and the second sample discharge sub conduit which is connected to the four-way cock being connected to the sampling bomb discharge conduit.

2. Apparatus according to claim 1, characterized in that the sampling bomb space, the sampling bomb supply conduit and the sampling bomb discharge conduit, the four-way cock and the second sample supply sub conduit and the second sample discharge sub conduit which are connected to the four-way cock are integrated in one part.

3. Apparatus according to claim 2, characterized in that the one part contains a cock knob for controlling the four-way cock, which cock knob is provided with a spring-back mechanism.

4. Apparatus according to claim1, characterized in that the four-way cock is a four-way ball valve.

5. Apparatus according to claim 1, characterized in that the fluid supply valve and the fluid discharge valve are each a multi-stage cock with at least three gates.

6. Apparatus according to claim5, characterized in that both multi-stage cocks have common control.

7. Apparatus for taking a sample of a fluid enclosed in a container, which apparatus is provided with a sampling station which is connectable to the container via a fluid supply conduit and a fluid discharge conduit, with a sample supply conduit connected by a fluid supply valve to the fluid supply conduit and a sample discharge conduit connected by a fluid discharge valve to the fluid discharge conduit, said fluid supply valve and said fluid discharge valve each being a multi-stage cock with at least three gates, a sampling bomb for containing the fluid sample, which sampling bomb comprises a sampling bomb space, a sampling bomb supply opening and a sampling bomb discharge opening, which are connectable to the sample supply conduit and the sample discharge conduit, respectively, and with a four-way cock, in one of the two positions of the four-way cock the fluid supply conduit being connected to the sampling bomb supply opening and the fluid discharge conduit being connected to the sampling bomb discharge opening, characterized in that the sampling bomb supply opening and the sampling bomb discharge opening are firmly connected to the four-way cock by a sampling bomb supply conduit and a sampling bomb discharge conduit, respectively, that the sample supply conduit is formed by a first sample supply sub conduit having a first end connected to the fluid supply valve and a second end comprising coupling elements and by a second sample supply sub conduit having a first end with coupling elements for coupling to the coupling elements of the first sample supply sub conduit and a second end firmly connected to the four-way cock, that the sample discharge conduit is formed by a first sample discharge sub conduit having a first end connected to the fluid discharge valve and a second end comprising coupling elements and by a second sample discharge sub conduit having a first end with coupling elements for coupling to the coupling elements of the first sample discharge sub conduit and a second end firmly connected to the four-way cock, in a first position of the four-way cock the second sample supply sub conduit which is connected to the four-way cock being connected to the second sample discharge sub conduit which is connected to the four-way cock and the sampling bomb supply conduit with the sampling bomb discharge conduit, and in a second position of the four-way cock the second sample supply sub conduit which is connected to the four-way cock being connected to the sampling bomb supply conduit and the Second sample discharge sub conduit which is connected to the four-way cock being connected to the sampling bomb discharge conduit.

8. Apparatus according to claim 7, characterized in that both multi-stage cocks have a common control.

9. Apparatus according to claim 7, characterized in that the four-way cock is a four-way ball valve.

10. Apparatus according to claim 7, characterized in that the sampling bomb, the sampling bomb supply conduit, the sampling bomb discharge conduit, the four-way cock, the second sample supply sub conduit and the second sample discharge sub conduit are integrated in one part.

11. Apparatus according to claim 10, characterized in that the one part contains a cock knob for controlling the four-way cock, which cock knob is provided with a spring-back mechanism.

\* \* \* \* \*